(12) United States Patent
Minamitani et al.

(10) Patent No.: US 11,248,222 B2
(45) Date of Patent: Feb. 15, 2022

(54) METHOD FOR CONTROLLING ENZYME PRODUCTIVITY OF MICROORGANISMS

(71) Applicants: Amano Enzyme Inc., Nagoya (JP); National University Corporation Yamagata University, Yamagata (JP)

(72) Inventors: Yasushi Minamitani, Yonezawa (JP); Toshiyuki Sugiura, Kitanagoya (JP)

(73) Assignees: AMANO ENZYME INC., Nagoya (JP); National University Corporation Yamagata University, Yamagata (JP)

( * ) Notice: Subject to any disclaimer, the term of this patent is extended or adjusted under 35 U.S.C. 154(b) by 164 days.

(21) Appl. No.: 16/079,682

(22) PCT Filed: Feb. 20, 2017

(86) PCT No.: PCT/JP2017/006238
§ 371 (c)(1),
(2) Date: Aug. 24, 2018

(87) PCT Pub. No.: WO2017/146009
PCT Pub. Date: Aug. 31, 2017

(65) Prior Publication Data
US 2019/0055539 A1 Feb. 21, 2019

(30) Foreign Application Priority Data
Feb. 24, 2016 (JP) .............................. JP2016-033589

(51) Int. Cl.
| | |
|---|---|
| *C12N 13/00* | (2006.01) |
| *C12N 9/00* | (2006.01) |
| *C12N 9/16* | (2006.01) |
| *C12N 9/24* | (2006.01) |
| *C12N 9/26* | (2006.01) |
| *C12N 9/28* | (2006.01) |
| *C12N 9/42* | (2006.01) |
| *C12N 9/48* | (2006.01) |
| *C12M 1/42* | (2006.01) |
| *C12M 1/00* | (2006.01) |

(52) U.S. Cl.
CPC .............. *C12N 13/00* (2013.01); *C12M 1/42* (2013.01); *C12M 21/14* (2013.01); *C12M 35/02* (2013.01); *C12N 9/00* (2013.01); *C12N 9/16* (2013.01); *C12N 9/2402* (2013.01); *C12N 9/2408* (2013.01); *C12N 9/2417* (2013.01); *C12N 9/2445* (2013.01); *C12N 9/48* (2013.01); *C12N 9/485* (2013.01); *C12Y 302/01001* (2013.01); *C12Y 302/0102* (2013.01); *C12Y 302/01021* (2013.01); *C12Y 302/01022* (2013.01); *C12Y 302/01023* (2013.01); *C12Y 304/11001* (2013.01); *C12Y 304/11007* (2013.01)

(58) Field of Classification Search
CPC ... C12N 13/00; C12N 9/16; C12Y 302/01001
See application file for complete search history.

(56) References Cited

U.S. PATENT DOCUMENTS

| | | | | |
|---|---|---|---|---|
| 2004/0097715 | A1* | 5/2004 | Teissie | ................... C12N 13/00 530/412 |
| 2012/0135468 | A1* | 5/2012 | Katase | ........... C12Y 302/01023 435/72 |

FOREIGN PATENT DOCUMENTS

| | | |
|---|---|---|
| JP | 06-277060 A | 10/1994 |
| JP | 09-322761 A | 12/1997 |
| JP | 2004-511257 A | 4/2004 |
| JP | 2008-523789 A | 7/2008 |
| JP | 2012-213353 A | 11/2012 |
| JP | 2013-027360 A | 2/2013 |
| JP | 2013-236600 A | 11/2013 |
| JP | 2014-511257 A | 5/2014 |
| JP | 2015-528705 A | 10/2015 |
| JP | 2016-019529 A | 2/2016 |
| WO | 2002/033065 A1 | 4/2002 |
| WO | 2011/004654 A1 | 1/2011 |
| WO | 2012/097050 A1 | 7/2012 |
| WO | 2012/133804 A1 | 10/2012 |
| WO | 2014/020141 A1 | 2/2014 |

OTHER PUBLICATIONS https://en.wikipedia.org/wiki/Damped_wave (Year: 2020).*
U.S. Appl. No. 15/577,815, filed 2017.*
https://www.btxonline.com/media/wysiwyg/education_page/Electroporation%20Optimization%20Guide.pdf (Year: 2021).*
https://www.btxonline.com/media/wysiwyg/education_page/Electroporation%20Crossover%20Guide.pdf (Year: 2021).*
T. Saito et al., "Effects of Electrical Stimulation on Edible Mushroom Yield and Laccase Activity," The Papers of Technical Meeting, IEE Japan, 2011, PPT-11, pp. 61-65. (cited in the ISR; Relevancy of the reference is stated in the written opinion).
J-A. Ewe et al., "Enhanced growth of lactobacilli and bioconversion of isoflavones in biotin-supplemented soymilk by electroporation," International Journal of Food Sciences and Nutrition, 2012, vol. 63, No. 5, pp. 580-596. (cited in the ISR).
International Search Report dated May 9, 2017, issued for PCT/JP2017/006238.
Office Action issued in Japanese Patent Application No. JP 2018-501681, dated Mar. 9, 2021.
Office Action dated Oct. 26, 2021 issued in the corresponding Japanese patent application No. 2018-501681 with its English Machine Translation.
Young et al., J. Microbiol. Biotechnol., 2008, 18(3), 545-551.

* cited by examiner

*Primary Examiner* — Ruth A Davis
(74) *Attorney, Agent, or Firm* — Locke Lord LLP; James E. Armstrong, IV; Nicholas J. DiCeglie, Jr.

(57) ABSTRACT

An object of the present invention is to provide a novel method for controlling enzyme productivity of a microorganism. A pulsed electric field is applied to a microorganism to control the enzyme productivity of the microorganism.

21 Claims, 2 Drawing Sheets

METHOD FOR CONTROLLING ENZYME PRODUCTIVITY OF MICROORGANISMS

TECHNICAL FIELD

The present invention relates to an application of a pulsed electric field to an enzyme production system. More specifically, the present invention relates to a method for controlling enzyme productivity of a microorganism by utilizing a pulsed electric field. The present application claims priority based on Japanese Patent Application No. 2016-033589 filed on Feb. 24, 2016, the entire contents of which are incorporated herein by reference.

BACKGROUND ART

Generally, in order to produce an enzyme using a microorganism, a microorganism is cultured under suitable culture conditions using suitable medium components, and then the produced enzyme is collected. Since microorganisms usually produce various enzymes, when it is desired to obtain a target enzyme more or to inhibit the production of a specific enzyme, medium components and culture conditions are changed to control the enzyme productivity, that is, the amount and composition (balance) of the enzyme to be produced. However, especially, with respect to the change of the medium components, various regulations, allergenicity, residual agrichemicals, harmful substances, contaminants, danger, stable supply aspect, cost aspect, etc. impose limitations on choice, so that usable components are restricted in many cases. Therefore, changing the medium generally requires a lot of labor, and it is not always possible to set the optimum medium. In addition, it is often necessary to reset the culture conditions in accordance with the change of the medium components.

Also, the enzyme productivity is controlled by using gene recombination technology. However, it is necessary to screen a specific microorganism matching the purpose from an enormous number of microorganism populations in which the genes have been modified. In addition, the medium components and culture conditions suitable for culture of the microorganism often change together with the gene modification, and it is sometimes necessary to study the culture medium and culture conditions again.

Techniques utilizing a pulsed electric field, for example, in microorganism and cell modification/control are cited below (Patent Literatures 1 to 3).

CITATION LIST

Patent Literature

Patent Literature 1: Japanese Unexamined Patent Application Publication No. H06-277060
Patent Literature 2: Japanese Unexamined Patent Application Publication No. 2012-213353
Patent Literature 3: Japanese Unexamined Patent Application Publication No. 2013-236600 A

SUMMARY OF INVENTION

Technical Problem

Although there are several methods for controlling the enzyme productivity as mentioned above, any of the methods requires much labor and time, and, in many cases, cannot sufficiently achieve the object. If the enzyme productivity can be controlled without changing the culture medium components or culture conditions and further without gene modification of microorganisms, such control will be a general-purpose and highly effective enzyme production technique.

Solution to Problem

The present inventors have earnestly studied to solve the above problems. Specifically, focusing on a pulsed electric field, the present inventors have studied the possibility of its application to enzyme productivity control. Although there are examples using a pulsed electric field in the release of useful substances in microorganism cells (Patent Literature 1), the modification of microorganisms (Patent Literature 2), and the control of the activity of microorganisms (Patent Literature 3), there has not been reported any example using a pulsed electric field in the control of the enzyme productivity of microorganisms.

As a result of applying a pulsed electric field to various microorganisms to examine the effects of the pulsed electric field, there has been observed a phenomenon that, even when the same microorganism strain, the same medium, and, further, the same culture conditions are employed, the enzyme productivity changes depending on the presence or absence of the pulsed electric field application and on the conditions for such application. That is, it has been found that, by using a pulsed electric field, the enzyme productivity can be controlled without changing the composition of the medium and the culture conditions and without gene modification. The following inventions are mainly based on the above findings.

[1] A method for controlling the enzyme productivity of a microorganism characterized by applying a pulsed electric field to a microorganism.

[2] The method according to [1], comprising the step of applying the pulsed electric field to the culture solution during culture of the microorganism.

[3] The method according to [2], wherein the culture solution circulates in an electrode part that generates the pulsed electric field during culture.

[4] The method according to [2] or [3], wherein the pulsed electric field is repeatedly applied during culture.

[5] The method according to any one of [1] to [4], wherein the pulse waveform of the pulsed electric field is a damped oscillation waveform.

[6] The method according to any one of [1] to [5], wherein the field strength of the pulsed electric field is 10 kV/cm to 50 kV/cm.

[7] The method according to any one of [1] to [6], wherein the production amount of one or more enzymes selected from the group consisting of amylase, glucosidase, galactosidase, cellulase, esterase, lipase, protease, phosphatase, peptidase, nuclease, deaminase, oxidase, dehydrogenase, glutaminase, pectinase, catalase, dextranase, transglutaminase, protein deamidase, and pullulanase is controlled.

[8] The method according to any one of [1] to [6], wherein the production amount of one or more enzymes selected from the group consisting of α-amylase, α-glucosidase, β-glucosidase, α-galactosidase, β-galactosidase, cellulase, esterase, lipase, protease, acid phosphatase, alkaline phosphatase, leucine peptidase, alanine aminopeptidase, PPL aminopeptidase, and SAPA aminopeptidase is controlled.

[9] The method according to any one of [1] to [8], wherein the microorganism is a microorganism selected from the group consisting of filamentous fungi, actinomycetes, yeast, and bacteria.

[10] The method according to any one of [1] to [8], wherein the microorganism is a microorganism selected from the group consisting of the genus *Aspergillus*, the genus *Mucor*, the genus *Rhizomucor*, the genus *Rhizopus*, the genus *Penicillium*, the genus *Trametes*, the genus *Streptomyces*, the genus *Candida*, the genus *Saccharomyces*, the genus *Sporobolomyces*, the genus *Kluyveromyces*, the genus *Pichia*, the genus *Cryptococcus*, the genus *Bacillus*, the genus *Streptococcus*, the genus *Pseudomonas*, the genus *Burkholderia*, the genus *Clostridium*, the genus *Myrothecium*, the genus *Klebsiella*, the genus *Chryseobacterium*, and the genus *Escherichia*.

[11] The method according to any one of [1] to [8], wherein the microorganism is a microorganism selected from the group consisting of *Aspergillus oryzae*, *Aspergillus niger*, *Mucor javanicus*, *Bacillus subtilis*, *Bacillus amyloliquefaciens*, *Bacillus circulans*, *Streptomyces griseus*, and *Streptomyces thermocarboxydus*.

[12] The method according to any one of [1] to [6], wherein the control of the enzyme productivity is any of the following (1) to (8):

(1) control in which the microorganism is *Aspergillus oryzae*, the application of the pulsed electric field is carried out in a logarithmic phase and/or stationary phase during culture, and the production amount of one or more enzymes selected from the group consisting of α-amylase, α-galactosidase, β-galactosidase, protease, leucine aminopeptidase, PPL aminopeptidase, and esterase is up-regulated; control in which the application of the pulsed electric field is carried out in an induction phase during culture, and the production amount of one or more enzymes selected from the group consisting of α-amylase, α-glucosidase, β-glucosidase, α-galactosidase, leucine aminopeptidase, and esterase is down-regulated; or control in which the application of the pulsed electric field is carried out in the logarithmic phase and/or stationary phase during culture, and the production amount of SAPA aminopeptidase is down-regulated;

(2) control in which the microorganism is *Aspergillus niger*, the application of the pulsed electric field is carried out in the stationary phase during culture, and the production amount of α-amylase and/or protease is up-regulated;

(3) control in which the microorganism is *Mucor javanicus*, the application of the pulsed electric field is carried out in the logarithmic phase and/or stationary phase during culture, and the production amount of α-amylase and/or β-glucosidase is up-regulated;

(4) control in which the microorganism is *Bacillus subtilis*, the application of the pulsed electric field is carried out in the logarithmic phase during culture, and the production amount of leucine aminopeptidase is up-regulated;

(5) control in which the microorganism is *Bacillus amyloliquefaciens*, the application of the pulsed electric field is carried out in the logarithmic phase and/or stationary phase during culture, and the production amount of lipase is up-regulated or the production amount of cellulase is down-regulated;

(6) control in which the microorganism is *Bacillus circulans*, the application of the pulsed electric field is carried out in the logarithmic phase during culture, and the production amount of β-galactosidase is up-regulated;

(7) control in which the microorganism is *Streptomyces griseus*, the application of the pulsed electric field is carried out in the logarithmic phase and/or stationary phase during culture, and the production amount of β-glucosidase is up-regulated or the production amount of α-amylase is down-regulated; and (8) control in which the microorganism is *Streptomyces thermocarboxydus*, the application of the pulsed electric field is carried out in the logarithmic phase during culture, and the production amount of protease is up-regulated.

[13] The method according to any one of [1] to [6] and [9] to [11], wherein the application of the pulsed electric field is carried out in the induction phase during culture, and the production amount of β-galactosidase is up-regulated.

[14] The method according to any one of [1] to [6] and [9] to [11], wherein the application of the pulsed electric field is carried out in the logarithmic phase during culture, and the production amount of one or more enzymes selected from the group consisting of α-amylase, α-galactosidase, β-glucosidase, β-galactosidase, protease, leucine peptidase, PPL aminopeptidase, and lipase is up-regulated.

[15] The method according to any one of [1] to [6] and [9] to [11], wherein the application of the pulsed electric field is carried out in the stationary phase during culture, and the production amount of α-amylase and/or protease is up-regulated.

[16] The method according to any one of [1] to [6], wherein the microorganism is *Aspergillus oryzae*, the application of the pulsed electric field is carried out in the logarithmic phase during culture, and the production amount of protease is up-regulated.

[17] The method according to any one of [1] to [6], wherein the microorganism is *Aspergillus oryzae*, the application of the pulsed electric field is carried out in the logarithmic phase during culture, and the production amount of peptidase is up-regulated.

[18] The method according to any one of [1] to [6], wherein the microorganism is *Aspergillus oryzae*, the application of the pulsed electric field is carried out in the induction phase and/or logarithmic phase during culture, and the production amount of β-galactosidase is up-regulated.

[19] The method according to any one of [1] to [6], wherein the microorganism is *Aspergillus oryzae*, the application of the pulsed electric field is carried out in the logarithmic phase during culture, and the production amount of α-galactosidase is up-regulated.

[20] The method according to any one of [1] to [6], wherein the microorganism is *Aspergillus oryzae*, the application of the pulsed electric field is carried out in the logarithmic phase during culture, and the production amount of α-amylase is up-regulated.

[21] The method according to any one of [1] to [6], wherein the microorganism is *Aspergillus niger*, the application of the pulsed electric field is carried out in the stationary phase during culture, and the production amount of protease is up-regulated.

[22] The method according to any one of [1] to [6], wherein the microorganism is *Aspergillus niger*, the application of the pulsed electric field is carried out in the stationary phase during culture, and the production amount of α-amylase is up-regulated.

[23] The method according to any one of [1] to [6], wherein the microorganism is *Bacillus subtilis*, the application of the pulsed electric field is carried out in the logarithmic phase during culture, and the production amount of peptidase is up-regulated.

[24] The microorganism according to any one of [1] to [6], wherein the microorganism is *Bacillus circulans*, the application of the pulsed electric field is carried out in the logarithmic phase during culture, and the production amount of β-galactosidase is up-regulated.

[25] A method for producing an enzyme composition, comprising a step of collecting an enzyme from a culture solution and/or cell bodies of a microorganism cultured by applying the method according to any one of [1] to [24].

[26] A method for producing an enzyme composition, comprising a step of removing cell bodies from a culture solution of a microorganism cultured by applying the method according to any one of [1] to [24].

[27] The production method according to [26], which further comprises the step of purifying the culture solution after removal of the cell bodies.

[28] An enzyme composition obtained by the production method according to any one of [25] to [27].

[29] A culture system for use in the method according to [2], comprising a culture vessel and a pulsed electric field generator whose electrode is provided inside the culture vessel.

[30] A culture system for use in the method according to [3] or [4], comprising: a culture vessel having a circulation channel; a liquid feeding means for feeding a liquid to the circulation channel; and a pulsed electric field generator, wherein an electrode part of the pulsed electric field generator is attached to the circulation channel.

DESCRIPTION OF EMBODIMENTS

1. Method for Controlling Enzyme Productivity, Culture System

A first aspect of the present invention relates to a method for controlling the enzyme productivity of a microorganism (hereinafter also referred to as "the control method of the present invention"). The control method of the present invention is characterized by applying a pulsed electric field to a microorganism for use in the production of an enzyme. Typically, a pulsed electric field is applied to a culture solution during culture of a microorganism to control enzyme productivity. For convenience of explanation, the microorganism to be subjected to the control method of the present invention is referred to as "producing strain" in some cases. Any conventional culture method may be employed, and, in general, a medium and culture conditions (temperature, oxygen concentration, etc.) suitable for growth and proliferation of the producing strain to be used are adopted.

The "enzyme productivity" is defined by the types of enzymes to be produced and the production amount of each of the enzymes. Therefore, when the control method of the present invention is applied, it is possible to increase or decrease the type of the enzyme to be produced, to change or adjust the compositional ratio or balance of the enzyme to be produced, to increase or decrease the production amount of a specific enzyme (one or more enzymes), to increase or decrease the total production amount of the enzyme, etc., according to the conditions to be adopted.

The application of the pulsed electric field to the culture solution during culture of the producing strain can be carried out, for example, via an electrode provided inside the culture vessel. Specifically, first, a culture system including a culture vessel and a pulsed electric field generator whose electrode is provided inside the culture vessel is constructed, and the culture of the producing strain is started using the system. Then, a pulsed electric field is generated at an appropriate time during culture and applied to the culture solution.

A culture system including: a culture vessel having a circulation channel; a liquid feeding means for feeding a liquid to the circulation channel; and a pulsed electric field generator, in which an electrode part of the pulsed electric field generator is attached to the circulation channel may be constructed to feed and circulate the culture solution into the circulation channel during culture, thereby applying the pulsed electric field. This system enables continuous processing, and the pulsed electric field can be efficiently applied.

Figure 1:
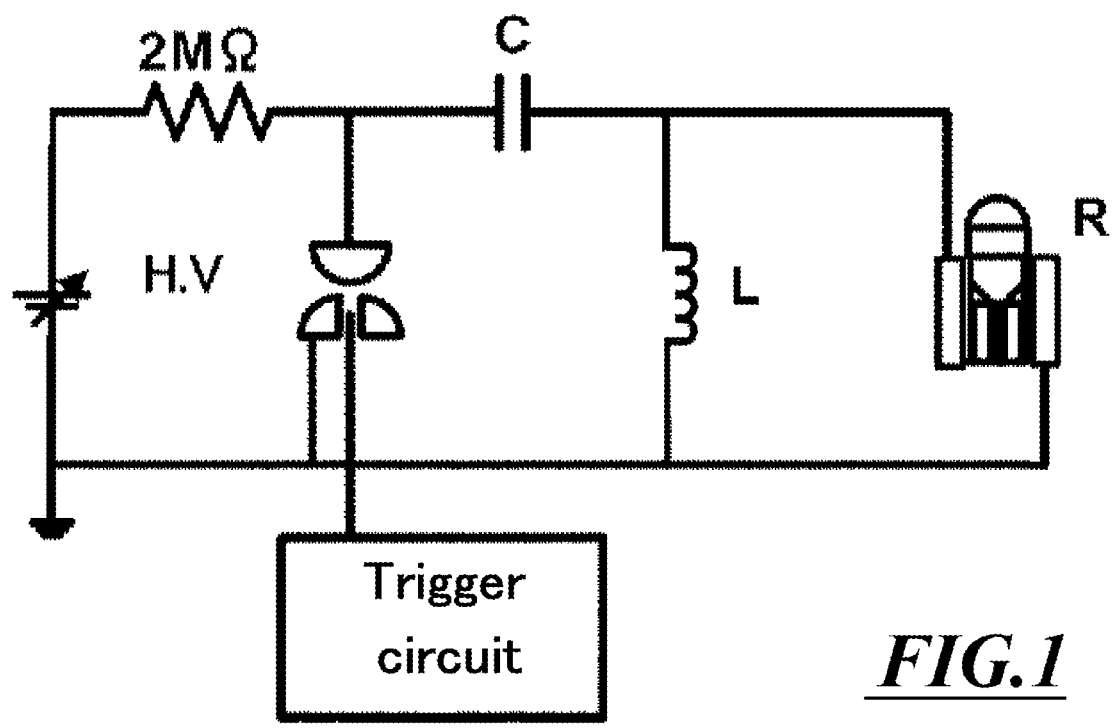
FIG. 1 shows an example of a pulsed electric field generator that can be used in the present invention.
Figure 2:
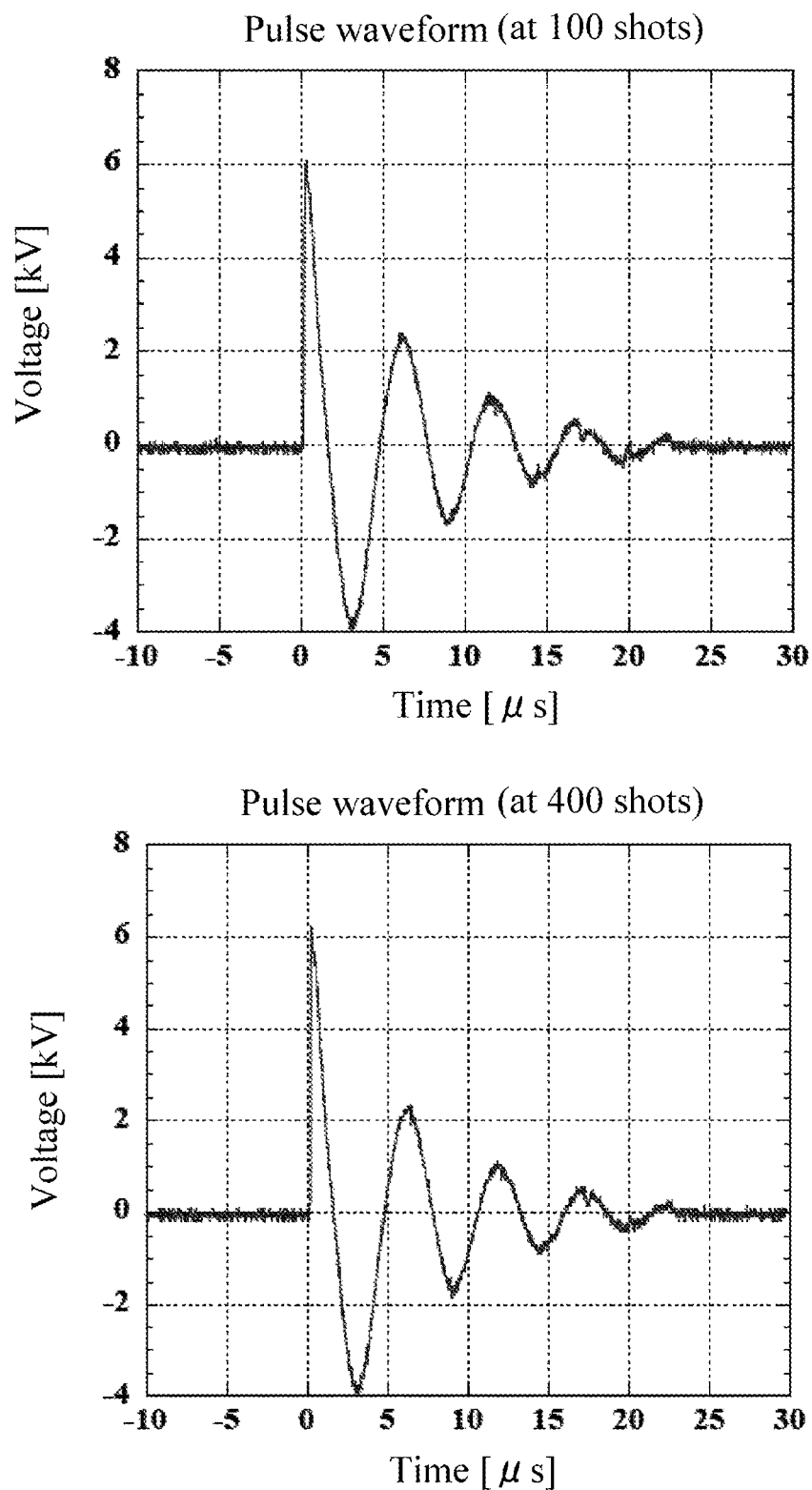
FIG. 2 shows an example of a pulse voltage waveform to be applied in the present invention. The number of applications is 100 shots in the upper figure and 400 shots in the lower figure.

FIG. 1 shows an example of a circuit of a pulsed electric field generator that can be used in the present invention. FIG. 2 shows an example of a pulse waveform to be output from this generator. This generator is composed of a high-voltage power source, a resistor (2 MΩ), a capacitor C, an inductance L, a trigatron gap switch, and a trigger circuit, and L and C constitute a parallel resonance circuit. The capacitor to be used is C=90 nF.

The principle of operation will be described. Initially, electric charge is charged in the capacitance C through the 2-MΩ resistor by the high-voltage power source. After charging, the electric charge charged in C is released into an RLC circuit by discharging with the gap switch. The current flowing in the RLC circuit forms a damped oscillation waveform due to the resonance of C and L, and is output to R which is a sample liquid connected in parallel.

In this pulsed electric field generator, the damped oscillation waveform as shown in FIG. 2 is output, but, by using a circuit with inductance L removed, it is also possible to output a damped waveform without oscillation. Such a generator can also be used in the present invention.

In order to minimize the influence of heat generated upon application of the pulsed electric field, it is advisable to install a water cooling device for cooling the electrode part. For example, the water cooling device is installed so that water flows into the electrode on the ground side with a pump to cool the electrode on the ground side. Furthermore, it is advisable to attach a cooling fin for heat exchange to the high pressure side so that heat can be easily released. With such a configuration, it is possible to suppress a rise in temperature of the sample during the application of an electric field.

When a pulsed electric field is applied to a cell, electric charge is accumulated in the cell membrane which acts as a capacitor in the electrical characteristics of the cell. This creates a potential difference between both sides of the cell membrane. When an electric field having field strength E is applied to a cell having a radius a, the potential difference Vm to be applied to a membrane located at a position at an angle θ with respect to the electric field direction is expressed by the following equation. The potential difference is proportional to the diameter of the cell and the field strength, and will be different depending on the position of the membrane with respect to the electric field direction.

$$Vm = 1.5 a \cdot E \cdot \cos\theta \qquad \text{[Formula 1]}$$

When this potential difference exceeds 1 V, dielectric breakdown occurs in the cell membrane. When dielectric breakdown occurs in the cell membrane, pores are formed in the cell. Pore formation in cells by a pulsed electric field is called electroporation. The potential difference of 1 V generates a very large electric field of $2 \times 10^6$ V/cm in the cell membrane. This pore is a reversible breakdown repaired by the cell itself unless it is too large, but if the field strength is increased or the pulse width is elongated to increase the energy to be applied, an irreversible breakdown which can no longer be repaired by the cell itself occurs in the cell membrane. Then, the tissue inside the cell flows to the outside, leading to necrosis of the cell. Since the larger the diameter of the cell is, the larger the potential difference to be applied to the cell membrane is, the cell membrane is destroyed easily. For example, since yeast has a larger diameter than that of *E. coli*, the potential difference to be applied to the cell membrane increases upon application of a pulsed electric field is increased.

The field strength of the pulsed electric field is not particularly limited as long as the enzyme productivity can be controlled, but is preferably 10 kV/cm to 50 kV/cm, preferably 10 kV/cm to 30 kV/cm, more preferably 20 kV/cm to 30 kV/cm. Also, it is preferable to apply the pulsed electric field a plurality of times (that is, repeatedly). Therefore, the number of applications is, for example, 10 shots (times) to 10,000 shots (times), preferably 100 shots (times) to 2,000 shots (times), more preferably 100 shots (times) to 1,500 shots (times). The number of repetitions can be set within a range in which the temperature of the solution does not rise, for example, within the range of 1 pps to 1000 pps.

As long as a useful enzyme is produced, the producing strain to be used in the present invention is not particularly limited. The "useful enzyme" is an enzyme having at least one industrial use (e.g., manufacturing industrial, food, medical, diagnostic, etc.). The present invention is a general-purpose method, and various microorganisms can be employed as the producing strain. Examples of the producing strains include filamentous fungi, actinomycetes, yeast, and bacteria, preferably the genus *Aspergillus* (more preferably, *Aspergillus oryzae* (e.g., RIB40 strain), the genus *Aspergillus niger* (e.g., NBRC 9455 strain)), the genus *Mucor* (more preferably, *Mucor javanicus* (e.g., IAM 6108 strain)), the genus *Rhizomucor*, the genus *Rhizopus*, the genus *Penicillium*, the genus *Trametes*, the genus *Streptomyces* (more preferably, *Streptomyces griseus* (e.g., IFO 12875 strain), *Streptomyces thermocarboxydus* (e.g., JCM 10367 strain)), the genus *Candida*, the genus *Saccharomyces*, the genus *Sporobolomyces*, the genus *Kluyveromyces*, the genus *Pichia*, the genus *Cryptococcus*, the genus *Bacillus* (more preferably, *Bacillus subtilis* (e.g., JCM 1465 strain), *Bacillus amyloliquefaciens* (e.g., IFO 3034 strain), *Bacillus circulans* (e.g., ATCC 21590 strain)), the genus *Streptococcus*, the genus *Pseudomonas*, the genus *Burkholderia*, the genus *Clostridium*, the genus *Myrothecium*, the genus *Klebsiella, Chryseobacterium*, and the genus *Escherichia* (more preferably, *Escherichia coli*). Two or more types of microorganisms may be co-cultured.

The producing strain produces one or more enzymes. Examples of the enzyme that can be produced by the producing strain, that is, the enzyme whose production amount is controlled by the method of the present invention include amylases (α-amylase, β-amylase, glucoamylase), glucosidases (α-glucosidase, β-glucosidase), galactosidase (α-galactosidase, β-galactosidase), proteases (acid protease, neutral protease, alkaline protease), peptidases (leucine peptidase, PPL (L-pyroglutamyl-L-phenylalanyl-L-leucine) aminopeptidase, SAPA (succinyl-L-alanyl-L-prolyl-L-alanine) aminopeptidase), lipase, esterase, cellulase, phosphatases (acid phosphatase, alkaline phosphatase), nuclease, deaminase, oxidase, dehydrogenase, glutaminase, pectinase, catalase, dextranase, transglutaminase, protein deamidase, and pullulanase.

As a result of detailed studies (see the Examples described later), the pulsed electric field applying conditions particularly effective for specific producing strains and the effects obtained thereby have been clarified, as shown below.

(1) Producing Strain *Aspergillus oryzae* (e.g., RIB 40 Strain)

Application time of pulsed electric field: induction phase, logarithmic phase, stationary phase Examples of enzymes to be produced: α-amylase, α-glucosidase, β-glucosidase, α-galactosidase, β-galactosidase, protease, leucine aminopeptidase, PPL aminopeptidase, esterase, SAPA aminopeptidase, acid phosphatase, alkaline phosphatase Examples of enzymes whose production amount increases: α-amylase (preferably, a pulsed electric field is applied in the logarithmic phase), α-galactosidase (preferably, a pulsed electric field is applied in the logarithmic phase), β-galactosidase (preferably, a pulsed electric field is applied a plurality of times from the induction phase to the logarithmic phase), protease (preferably, a pulsed electric field is applied in the logarithmic phase), leucine aminopeptidase (preferably, a pulsed electric field is applied in the logarithmic phase), PPL aminopeptidase (preferably, a pulsed electric field is applied in the logarithmic phase), esterase (preferably, a pulsed electric field is applied in the logarithmic phase)

Examples of enzymes whose production amount decreases: α-amylase (preferably, a pulsed electric field is applied in the induction phase), α-glucosidase (preferably, a pulsed electric field is applied in the induction phase), β-glucosidase (preferably, a pulsed electric field is applied from the induction phase to the logarithmic phase), α-galactosidase (preferably, a pulsed electric field is applied in the induction phase), leucine aminopeptidase (preferably, a pulsed electric field is applied in the induction phase), SAPA aminopeptidase (preferably, a pulsed electric field is applied from the logarithmic phase to the stationary phase), esterase (preferably, a pulsed electric field is applied in the induction phase)

(2) Producing Strain *Aspergillus niger* (e.g., NBRC 9455 Strain)

Application time of pulsed electric field: logarithmic phase, stationary phase

Examples of enzymes to be produced: α-amylase, α-glucosidase, β-glucosidase, α-galactosidase, β-galactosidase, protease, acid phosphatase, lipase Examples of enzymes whose production amount increases: α-amylase (preferably, a pulsed electric field is applied in the stationary phase), protease (preferably, a pulsed electric field is applied in the stationary phase)

Examples of enzymes whose production amount decreases: α-galactosidase (preferably, a pulsed electric field is applied in the stationary phase), β-galactosidase (preferably, a pulsed electric field is applied in the stationary phase)

(3) Producing Strain *Mucor javanicus* (e.g., IAM 6108 Strain)

Application time of pulsed electric field: logarithmic phase, stationary phase

Examples of enzymes to be produced: α-amylase, α-glucosidase, β-glucosidase, α-galactosidase, β-galactosidase, protease, leucine aminopeptidase, alanine aminopeptidase, lipase Examples of enzymes whose production amount increases: α-amylase (preferably, a pulsed electric field is applied in the stationary phase), β-glucosidase (preferably, a pulsed electric field is applied in the logarithmic phase)

(4) Producing Strain *Bacillus subtilis* (e.g., JCM 1465 Strain)

Application time of pulsed electric field: logarithmic phase

Examples of enzymes to be produced: α-amylase, α-glucosidase, protease, leucine aminopeptidase, alkaline phosphatase, lipase Examples of enzymes whose production amount increases: Leucine aminopeptidase (preferably, a pulsed electric field is applied in the logarithmic phase)

(5) Producing Strain *Bacillus amyloliquefaciens* (e.g., IFO 3034 Strain)

Application time of pulsed electric field: logarithmic phase, stationary phase

Examples of enzymes to be produced: α-amylase, α-glucosidase, protease, leucine aminopeptidase, alkaline phosphatase, lipase Examples of enzymes whose production amount increases: Lipase (preferably, a pulsed electric field is applied from the logarithmic phase to the stationary phase)

Examples of enzymes whose production amount decreases: Cellulase (preferably, a pulsed electric field is applied from the logarithmic phase to the stationary phase)

(6) Producing Strain *Bacillus circulans* (e.g., ATCC 21590 Strain)

Application time of pulsed electric field: logarithmic phase

Examples of enzymes to be produced: α-amylase, β-galactosidase, protease

Examples of enzymes whose production amount increases: β-galactosidase (preferably, a pulsed electric field is applied in the logarithmic phase)

(7) Producing Strain *Streptomyces griseus* (e.g., IFO 12875 Strain)

Application time of pulsed electric field: logarithmic phase, stationary phase

Examples of enzymes to be produced: α-amylase, β-glucosidase, protease

Examples of enzymes whose production amount increases: β-glucosidase (preferably, a pulsed electric field is applied in the logarithmic phase)

Examples of enzymes whose production amount decreases: α-amylase (preferably, a pulsed electric field is applied from the logarithmic phase to the stationary phase)

(8) Producing Strain *Streptomyces thermocarboxydus* (e.g., JCM 10367 Strain)

Application time of pulsed electric field: logarithmic phase

Examples of enzymes to be produced: α-amylase, protease

Examples of enzymes whose production amount increases: Protease (preferably, a pulsed electric field is applied in the logarithmic phase)

2. Method for Producing Enzyme Composition, Enzyme Composition

When the control method of the present invention is applied to an enzyme production system utilizing a microorganism, it shows enzyme productivity different from that when it is not applied. Therefore, it is possible to produce a characteristic enzyme composition. Therefore, a second aspect of the present invention provides a method for producing an enzyme composition (hereinafter also referred to as "the production method of the present invention") as a use of the control method of the present invention. The "enzyme composition" is a composition containing at least one type of enzyme. Therefore, a composition containing only one specific type of enzyme (having no substantial contaminating enzyme activity) also corresponds to the enzyme composition.

In one embodiment of the production method of the present invention, an enzyme is collected from a culture solution or cell bodies of a microorganism cultured by applying the control method of the present invention, or both. When the enzyme is collected from the culture solution, an enzyme composition can be obtained, for example, by removing insoluble matter through filtration, centrifugation, or the like of a culture supernatant, and, thereafter, appropriately combining concentration by an ultrafiltration membrane, salting-out such as ammonium sulfate precipitation, dialysis, various types of chromatography with ion exchange resins, etc. for separation and purification. On the other hand, when the enzyme is collected from the cell bodies, an enzyme composition can be obtained, for example, by crushing the cell bodies through pressure treatment, ultrasonic treatment, or the like, followed by separation and purification in a similar manner as described above. After preliminary collection of the cell bodies from the culture solution through filtration, centrifugation, or the like, the above-mentioned series of steps (crushing, separation, and purification of the cell bodies) may be carried out.

Hereinafter, Examples (experimental examples) of the present invention will be illustrated, but the present invention is not limited by the Examples.

EXAMPLES

A pulsed electric field was applied to various microorganisms to examine the effects and influences on enzyme productivity.

1. Test Microorganism Strain

*Aspergillus oryzae* RIB 40 strain, *Aspergillus niger* NBRC 9455 strain, *Mucor javanicus* IAM 6108 strain, *Bacillus subtilis* JCM 1465, *Bacillus amyloliquefaciens* IFO 3034 strain, *Bacillus circulans* ATCC 21590 strain, *Streptomyces Griseus* IFO 12875 strain, *Streptomyces thermocarboxydus* JCM 10367 strain 2. Experimental Method Each microorganism strain was cultured, and a pulsed electric field was applied at a predetermined time (induction phase, early stage of logarithmic phase, latter stage of logarithmic phase, stationary phase). Thereafter, a culture solution or cell bodies was/were recovered at a predetermined time to prepare a sample for measuring the enzyme activity. Regarding the culture solution, a supernatant was recovered by centrifugation and used as an extracellular sample. Regarding the contents of cell bodies, a precipitate by centrifugation was crushed by aluminum oxide treatment, and the centrifuged supernatant was recovered to prepare an intracellular sample. Various enzyme activities were measured for each of the samples. Hereinafter, the medium/culture conditions and the conditions for applying the pulsed electric field are indicated for each microorganism strain.

(1) *Aspergillus oryzae* RIB 40 Strain

Medium/culture conditions: 50% bran medium, cultured at 28° C.

High electric field pulse application condition: field strength: 15 kV/cm or 30 kV/cm; number of applications: 100 shots; number of repetitions: 1 pps; waveform: damped oscillation wave (2) *Aspergillus niger* NBRC 9455 Strain
Medium/culture conditions: 50% bran medium, cultured at 28° C.
High electric field pulse application condition: field strength: 15 kV/cm; number of applications: 100 shots; number of repetitions: 1 pps; waveform: damped oscillation wave (3) *Mucor javanicus* IAM 6108 Strain
Medium/culture conditions: 50% bran medium, cultured at 28° C.
High electric field pulse application condition: field strength: 15 kV/cm; number of applications: 100 shots; number of repetitions: 1 pps; waveform: damped oscillation wave (4) *Bacillus subtilis* JCM 1465 Strain
Medium/culture conditions: SCD medium, cultured at 28° C.
High electric field pulse application condition: field strength: 15 kV/cm or 30 kV/cm; number of applications: 100 shots; number of repetitions: 1 pps; waveform: damped oscillation wave (5) *Bacillus amyloliquefaciens* IFO 3034 Strain
Medium/culture conditions: SCD medium, cultured at 28° C.
High electric field pulse application condition: field strength: 15 kV/cm or 30 kV/cm; number of applications: 100 shots; number of repetitions: 1 pps; waveform: damped oscillation wave (6) *Bacillus amyloliquefaciens* IFO 3034 Strain
Medium/culture conditions: YM broth medium, cultured at 28° C.
High electric field pulse application condition: field strength: 30 kV/cm; number of applications: 100 shots; number of repetitions: 1 pps; waveform: damped oscillation wave (7) *Bacillus circulans* ATCC 21590 Strain
Medium/culture conditions: YM broth medium, cultured at 28° C.
High electric field pulse application condition: field strength: 30 kV/cm; number of applications: 100 shots; number of repetitions: 1 pps; waveform: damped oscillation wave (8) *Streptomyces griseus* IFO 12875 Strain
Medium/culture conditions: YM broth medium, cultured at 28° C.
High electric field pulse application condition 1: field strength: 30 kV/cm; number of applications: 100 shots; number of repetitions: 1 pps; waveform: damped oscillation wave
High electric field pulse application condition 2: field strength: 30 kV/cm; number of applications: 400 shots; number of repetitions: 3 pps; waveform: damped oscillation wave (9) *Streptomyces thermocarboxydus* JCM 10367 Strain
Medium/culture conditions: YM broth medium, cultured at 28° C.
High electric field pulse application condition 1: field strength: 30 kV/cm; number of applications: 100 shots; number of repetitions: 1 pps; waveform: damped oscillation wave
High electric field pulse application condition 2: field strength: 30 kV/cm; number of applications: 400 shots; number of repetitions: 3 pps; waveform: damped oscillation wave For each microorganism strain, the relationship between the culture time and the proliferation time was defined as follows.

<Filamentous Fungi (*Aspergillus oryzae*, *Aspergillus niger*, *Mucor javanicus*)>
4 hours after culture: induction phase
18 hours after culture, 22 hours after culture: early stage of logarithmic phase
39 hours after culture, 44 hours after culture: latter stage of logarithmic phase
66 hours after culture: stationary phase (resting phase)

<*Bacillus subtilis*, *Bacillus amyloliquefaciens*>
21 hours after culture, 22 hours after culture: early stage of logarithmic phase
43 hours after culture, 44 hours after culture: latter stage of logarithmic phase
65 hours after culture: stationary phase (resting phase)

<*Bacillus circulans*>
43 hours after culture, 44 hours after culture: early stage of logarithmic phase
65 hours after culture: latter stage of logarithmic phase
*Since the amount of the inoculated bacterial cells was small and the growth was delayed, it was different from other *Bacillus* bacteria.

<Actinomycetes (*Streptomyces griseus*, *Streptomyces thermocarboxydus*)>
21 hours after culture: early stage of logarithmic phase
43 hours after culture: latter stage of logarithmic phase
65 hours after culture: stationary phase (resting phase)

The method for measuring the activity of each of the enzymes was as follows.

<Buffer Used>
100 mmol/L acetate buffer pH 4.2
100 mmol/L acetate buffer pH 5.0
100 mmol/L phosphate buffer pH 7.0
100 mmol/L PIPES buffer pH 7.1
100 mmol/L borate buffer pH 9.2

<α-Amylase>
Soluble starch (manufactured by Merck) was dissolved in a buffer so as to be 1.0 g/dL to prepare a substrate solution. To this, an appropriately diluted enzyme sample solution was added in a 1/5 amount of the substrate solution to initiate the reaction. A 20 mmol/L iodine solution was added in a 1/6 amount of the reaction solution to measure the color development through an iodine starch reaction by absorbance at 540 nm, and the enzyme activity was estimated as a relative value to the measurement value of a culture sample to which no pulsed electric field was applied under the respective conditions.

<α-Glucosidase>
p-Nitrophenyl α-D-glucopyranoside (manufactured by Sigma-Aldrich) was dissolved in a buffer so as to be 12 mmol/L to prepare a substrate solution. To this, an appropriately diluted enzyme sample solution was added in a 1/4 amount of the substrate solution to initiate the reaction. A 1 g/dL sodium carbonate solution was added in an equal amount of the reaction solution to measure the color development of liberated p-nitrophenol by absorbance at 420 nm, and the enzyme activity was estimated as a relative value to the measurement value of a culture sample to which no pulsed electric field was applied under the respective conditions.

<β-Glucosidase>
p-Nitrophenyl β-D-glucopyranoside (manufactured by Sigma-Aldrich) was dissolved in a buffer so as to be 12 mmol/L to prepare a substrate solution. To this, an appropriately diluted enzyme sample solution was added in a 1/4 amount of the substrate solution to initiate the reaction. A 1 g/dL sodium carbonate solution was added in an equal amount of the reaction solution to measure the color development of liberated p-nitrophenol by absorbance at 420 nm, and the enzyme activity was estimated as a relative value to the measurement value of a culture sample to which no pulsed electric field was applied under the respective conditions.

<α-Galactosidase> p-Nitrophenyl α-D-galactopyranoside (manufactured by Sigma-Aldrich) was dissolved in a buffer so as to be 12 mmol/L to prepare a substrate solution. To this, an appropriately diluted enzyme sample solution was added in a 1/4 amount of the substrate solution to initiate the reaction. A 1 g/dL sodium carbonate solution was added in an equal amount of the reaction solution to measure the color development of liberated p-nitrophenol by absorbance at 420 nm, and the enzyme activity was estimated as a relative value to the measurement value of a culture sample to which no pulsed electric field was applied under the respective conditions.

<β-Galactosidase> p-Nitrophenyl β-D-galactopyranoside (manufactured by Sigma-Aldrich) was dissolved in a buffer so as to be 12 mmol/L to prepare a substrate solution. To this, an appropriately diluted enzyme sample solution was added in a 1/4 amount of the substrate solution to initiate the reaction. A 1 g/dL sodium carbonate solution was added in an equal amount of the reaction solution to measure the color development of liberated p-nitrophenol by absorbance at 420 nm, and the enzyme activity was estimated as a relative value to the measurement value of a culture sample to which no pulsed electric field was applied under the respective conditions.

<Cellulase>

Cellazyme C tablets (manufactured by Cellazyme) were suspended in 10 mL of a buffer per tablet to prepare a substrate solution. To this, an appropriately diluted enzyme sample solution was added in a 1/13 amount of the substrate solution to initiate the reaction. After completion of the reaction, the reaction solution was filtered through a cellulose filter, and an azo dye-bound low molecule contained in the filtrate was measured by absorbance at 590 nm. The enzyme activity was estimated as a relative value to the measurement value of a culture sample to which no pulsed electric field was applied under the respective conditions.

<Esterase> p-Nitrophenyl-acetate (manufactured by Wako Pure Chemical Industries, Ltd.) was dissolved in a buffer containing 30 g/dL ethanol so as to be 12 mmol/L to prepare a substrate solution. To this, an appropriately diluted enzyme sample solution was added in a 1/4 amount of the substrate solution to initiate the reaction. The color development of liberated p-nitrophenol was measured by absorbance at 420 nm, and the enzyme activity was estimated as a relative value to the measurement value of a culture sample to which no pulsed electric field was applied under the respective conditions.

<Lipase> p-Nitrophenyl-stearate (manufactured by Sigma-Aldrich) was dissolved in a buffer containing 30 g/dL ethanol so as to be 0.31 mmol/L to prepare a substrate solution. To this, an appropriately diluted enzyme sample solution was added in a 1/4 amount of the substrate solution to initiate the reaction. The color development of liberated p-nitrophenol was measured by absorbance at 420 nm, and the enzyme activity was estimated as a relative value to the measurement value of a culture sample to which no pulsed electric field was applied under the respective conditions.

<Protease>

Casein (manufactured by Calbiochem) was dissolved or suspended in a buffer so as to be 0.1 g/dL to prepare a substrate solution. To this, an appropriately diluted enzyme sample solution was added in a 1/10 amount of the substrate solution to initiate the reaction. After addition of a 400 mmol/L trichloroacetic acid solution in an equivalent amount of the substrate solution, the solution was centrifuged at 15,000 rpm for 10 minutes to obtain a supernatant. The solubilized peptide in the resultant supernatant was measured by absorbance at 280 nm, and the enzyme activity was estimated as a relative value to the measurement value of a cultured sample to which no pulsed electric field was applied under the respective conditions.

<Phosphatase> p-Nitrophenyl-phosphate (manufactured by Wako Pure Chemical Industries, Ltd.) was dissolved in a buffer so as to be 2 mmol/L to prepare a substrate solution. To this, an appropriately diluted enzyme sample solution was added in a 1/5 amount of the substrate solution to initiate the reaction. A 1 g/dL sodium carbonate solution was added in an equal amount of the reaction solution to measure the color development of liberated p-nitrophenol by absorbance at 420 nm, and the enzyme activity was estimated as a relative value to the measurement value of a culture sample to which no pulsed electric field was applied under the respective conditions.

<Leucine Aminopeptidase>

L-Leucine-p-nitroanilide (manufactured by Wako Pure Chemical Industries, Ltd.) was dissolved in a buffer containing 5 g/dL of dimethylsulfoxide (manufactured by Wako Pure Chemical Industries, Ltd.) so as to be 4.8 mmol/L to prepare a substrate solution. To this, an appropriately diluted enzyme sample solution was added in a 1/4 amount of the substrate solution to initiate the reaction. The color development of liberated p-nitroanilide was measured by absorbance at 450 nm, and the enzyme activity was estimated as a relative value with respect to the measurement value of a cultured sample to which no pulsed electric field was applied under the respective conditions.

<Alanine Aminopeptidase>

L-Alanine-p-nitroanilide (manufactured by Wako Pure Chemical Industries, Ltd.) was dissolved in a buffer containing 5 g/dL of dimethylsulfoxide (manufactured by Wako Pure Chemical Industries, Ltd.) so as to be 4.8 mmol/L to prepare a substrate solution. To this, an appropriately diluted enzyme sample solution was added in a 1/4 amount of the substrate solution to initiate the reaction. The color development of liberated p-nitroanilide was measured by absorbance at 450 nm, and the enzyme activity was estimated as a relative value with respect to the measurement value of a cultured sample to which no pulsed electric field was applied under the respective conditions.

<PPL Aminopeptidase>

L-Pyroglutamyl-L-phenylalanyl-L-leucine-p-nitroanilide (manufactured by Wako Pure Chemical Industries, Ltd.) was dissolved in 20 g/dL dimethylsulfoxide (manufactured by Wako Pure Chemical Industries, Ltd.) so as to be 2.4 mmol/L to prepare a substrate solution. To this, an appropriately diluted enzyme sample solution was added in a 1/4 amount of the substrate solution to initiate the reaction. The color development of liberated p-nitroanilide was measured by absorbance at 450 nm, and the enzyme activity was estimated as a relative value with respect to the measurement value of a cultured sample to which no pulsed electric field was applied under the respective conditions.

<SAPA Aminopeptidase>

Succinyl-L-alanyl-L-prolyl-L-alanine-p-nitroanilide (manufactured by Wako Pure Chemical Industries, Ltd.) was dissolved in a buffer containing 10 g/dL dimethylsulfoxide (manufactured by Wako Pure Chemical Industries, Ltd.) so as to be 2.4 mmol/L to prepare a substrate solution. To this, an appropriately diluted enzyme sample solution was added in a 1/4 amount of the substrate solution to initiate the reaction. The color development of liberated p-nitroanilide was measured by absorbance at 450 nm, and the enzyme activity was estimated as a relative value with respect to the measurement value of a cultured sample to which no pulsed electric field was applied under the respective conditions.

3. Experimental Results (1) *Aspergillus oryzae* RIB 40 Strain (Study on Application Time and Field Strength)

The following test groups with different application times and field strengths of the pulsed electric field were set.

(a) A pulsed electric field having field strength of 15 kV/cm was applied 4 hours after culture (induction phase).

(b) A pulsed electric field having field strength of 30 kV/cm was applied 4 hours after culture.

(c) A pulsed electric field having field strength of 15 kV/cm was applied 4 hours after culture and 18 hours after culture (early stage of logarithmic phase).

(d) A pulsed electric field having field strength of 30 kV/cm was applied 4 hours after culture and 18 hours after culture.

(e) A pulsed electric field having field strength of 15 kV/cm was applied 18 hours after culture.

(f) A pulsed electric field having field strength of 30 kV/cm was applied 18 hours after culture.

(g) A pulsed electric field having field strength of 15 kV/cm was applied 18 hours after culture and 39 hours after culture (latter stage of logarithmic phase).

(h) A pulsed electric field having field strength of 30 kV/cm was applied 18 hours after culture and 39 hours after culture.

The culture solution was recovered 88 hours after culture to prepare a sample, and various enzyme activities were measured. The measurement results are shown in the following table. The underline represents an increase in activity, and the double underline represents a decrease in activity.

TABLE 1

| Measurement item and pH at measurement | Field strength kV/cm | 4 hr (induction phase) | 4, 18 hr | 18 hr (early stage of logarithmic phase) | 18, 39 hr |
|---|---|---|---|---|---|
| α-Amylase pH 5.0 | 15 | 45% | 110% | 131% | 134% |
|  | 30 | — | — | — | — |
| α-Glucosidase pH 7.0 | 15 | 73% | 120% | 104% | 115% |
|  | 30 | 73% | 94% | 95% | 110% |
| β-Glucosidase pH 7.0 | 15 | 61% | 93% | 68% | 66% |
|  | 30 | 62% | 81% | 70% | 56% |
| α-Galactosidase pH 7.0 | 15 | 66% | 130% | 125% | 129% |
|  | 30 | 63% | 94% | 126% | 131% |
| β-Galactosidase pH 4.2 | 15 | 83% | 192% | 105% | 82% |
|  | 30 | 86% | 140% | 122% | 86% |
| Protease pH 4.2 | 15 | 93% | 114% | 103% | 133% |
|  | 30 | 89% | 102% | 93% | 125% |
| Protease pH 7.0 | 15 | 106% | 124% | 120% | 144% |
|  | 30 | 106% | 120% | 119% | 157% |
| Leucine aminopeptidase pH 5.0 | 15 | 72% | 119% | 127% | 169% |
|  | 30 | 67% | 91% | 102% | 182% |
| PPL aminopeptidase pH 7.0 | 15 | 94% | 122% | 132% | 166% |
|  | 30 | 89% | 114% | 122% | 174% |
| Esterase pH 7.0 | 15 | 58% | 94% | 125% | 101% |
|  | 30 | 61% | 75% | 124% | 114% |

Most of the enzyme production amounts decreased upon application of the pulsed electric field in the induction phase. On the other hand, the production amount of the α-amylase increased upon application of the pulsed electric field having field strength of 15 kV/cm in the logarithmic phase. In addition, the production amount of the α-galactosidase increased upon application of the pulsed electric field in the logarithmic phase. For β-galactosidase, the enzyme production amount increased upon application of the pulsed electric field a plurality of times from the induction phase to logarithmic phase. The production amounts of the proteases and peptidases increased upon application of the pulsed electric field in the logarithmic phase. No significant difference was observed in the change in enzyme production amount between the field strengths of 15 kV/cm and 30 kV/cm.

(2) *Aspergillus oryzae* RIB 40 Strain (Comparison Between Intracellular Enzyme and Extracellular Enzyme)

The following test groups with different application times of the pulsed electric field were set.

(a) A pulsed electric field having field strength of 15 kV/cm was applied 44 hours after culture (latter stage of logarithmic phase).

(b) A pulsed electric field having field strength of 15 kV/cm was applied 66 hours after culture (stationary phase).

The culture solution and cell bodies were recovered 88 hours after culture to prepare a sample, and various enzyme activities were measured. The measurement results are shown in the following table. The underline represents an increase in activity, and the double underline represents a decrease in activity.

TABLE 2

| Measurement item and pH at measurement | Field strength kV/cm | Sample | Application time and relative activity | |
|---|---|---|---|---|
| | | | 44 hr (latter stage of logarithmic phase) | 66 hr (stationary phase) |
| SAPA aminopeptidase pH 7.0 | 15 | Extra-cellular | 59% | 68% |
| | 15 | Intra-cellular | 59% | 68% |
| Acid phosphatase pH 5.0 | 15 | Extra-cellular | 114% | 90% |
| | 15 | Intra-cellular | 127% | 133% |

When the pulsed electric field was applied from the logarithmic phase to the stationary phase, the production amount of the peptidase decreased. Both of the enzymes showed equivalent relative activity intracellularly and extracellularly, indicating that the application of the pulsed electric field did not improve the enzyme extraction efficiency from the cells, but affected the enzyme productivity.

(3) *Aspergillus niger* NBRC 9455 Strain (Study on Application Time)

The following test groups with different application times of the pulsed electric field were set.

(a) A pulsed electric field having field strength of 15 kV/cm was applied 22 hours after culture (early stage of logarithmic phase).

(b) A pulsed electric field having field strength of 15 kV/cm field strength was applied 44 hours after culture (latter stage of logarithmic phase).

(c) A pulsed electric field having field strength of 15 kV/cm field strength was applied 66 hours after the culture (resting phase).

The culture solution was recovered 88 hours after culture to prepare a sample, and various enzyme activities were measured. The measurement results are shown in the following table. The underline represents an increase in activity, and the double underline represents a decrease in activity.

TABLE 3

| Measurement item and pH at measurement | Field strength kV/cm | Application time and relative activity | | |
|---|---|---|---|---|
| | | 22 hr (early stage of logarithmic phase) | 44 hr (latter stage of logarithmic phase) | 66 hr (stationary phase) |
| α-Amylase pH 5.0 | 15 | 106% | 107% | 137% |
| α-Amylase pH 7.1 | 15 | 124% | 126% | 137% |
| α-Amylase pH 9.2 | 15 | 96% | 112% | 166% |
| α-Glucosidase pH 7.0 | 15 | 102% | 90% | 96% |
| β-Glucosidase pH 7.1 | 15 | 100% | 88% | 117% |
| α-Galactosidase pH 7.1 | 15 | 84% | 88% | 56% |
| β-Galactosidase pH 5.0 | 15 | 83% | 85% | 66% |
| Protease pH 4.2 | 15 | 110% | 102% | 136% |
| Protease pH 7.0 | 15 | 111% | 105% | 162% |
| Protease pH 9.2 | 15 | 109% | 101% | 153% |
| Acid phosphatase pH 5.0 | 15 | 92% | 100% | 79% |
| Lipase pH 7.1 | 15 | 72% | 82% | 80% |
| Lipase pH 9.2 | 15 | 107% | 82% | 93% |

When the pulsed electric field was applied in the stationary phase, the production amount of the α-amylases increased. Likewise, when the pulsed electric field was applied in the stationary phase, the production amount of the proteases increased.

(4) *Mucor javanicus* IAM 6108 Strains (Study on Application Time)

The following test groups with different application times of the pulsed electric field were set.

(a) A pulsed electric field having field strength of 15 kV/cm was applied 22 hours after culture (early stage of logarithmic phase).

(b) A pulsed electric field having field strength of 15 kV/cm field strength was applied 44 hours after culture (latter stage of logarithmic phase).

(c) A pulsed electric field having field strength of 15 kV/cm field strength was applied 66 hours after the culture (resting phase).

The culture solution was recovered 88 hours after culture to prepare a sample, and various enzyme activities were measured. The measurement results are shown in the following table. The underline represents an increase in activity.

TABLE 4

| Measurement item and pH at measurement | Field strength kV/cm | Application time and relative activity | | |
|---|---|---|---|---|
| | | 22 hr (early stage of logarithmic phase) | 44 hr (latter stage of logarithmic phase) | 66 hr (stationary phase) |
| α-Amylase pH 5.0 | 15 | 94% | 107% | 128% |
| α-Amylase pH 7.1 | 15 | 89% | 103% | 118% |
| α-Amylase pH 9.2 | 15 | 95% | 107% | 128% |

TABLE 4-continued

| Measurement item and pH at measurement | Field strength kV/cm | Application time and relative activity | | |
|---|---|---|---|---|
| | | 22 hr (early stage of logarithmic phase) | 44 hr (latter stage of logarithmic phase) | 66 hr (stationary phase) |
| α-Glucosidase pH 7.0 | 15 | 124% | 88% | 102% |
| β-Glucosidase pH 7.1 | 15 | 139% | 97% | 87% |
| α-Galactosidase pH 7.0 | 15 | 103% | 113% | 113% |
| β-Galactosidase pH 5.0 | 15 | 90% | 93% | 106% |
| Protease pH 4.2 | 15 | 92% | 94% | 90% |
| Protease pH 7.0 | 15 | 88% | 98% | 94% |
| Protease pH 9.2 | 15 | 99% | 113% | 111% |
| Leucine aminopeptidase pH 7.0 | 15 | 107% | 115% | 108% |
| Alanine aminopeptidase pH 7.0 | 15 | 102% | 112% | 103% |
| Lipase pH 7.1 | 15 | 91% | 89% | 88% |
| Lipase pH 9.2 | 15 | 94% | 92% | 88% |

When the pulsed electric field was applied in the stationary phase, the production amount of the α-amylases increased. For the β-glucosidases, when the pulsed electric field was applied in the logarithmic phase, the enzyme production amount increased.

(5) *Mucor javanicus* IAM 6108 Strain (Comparison Between Intracellular and Extracellular Enzymes)

The following test groups with different application times of the pulsed electric field were set.

(a) A pulsed electric field having field strength of 15 kV/cm was applied 22 hours after culture (early stage of logarithmic phase).

(b) A pulsed electric field having field strength of 15 kV/cm field strength was applied 44 hours after culture (latter stage of logarithmic phase).

(c) A pulsed electric field having field strength of 15 kV/cm field strength was applied 66 hours after the culture (resting phase).

The culture solution and cell bodies were recovered 88 hours after culture to prepare a sample, and various enzyme activities were measured. The measurement results are shown in the following table.

TABLE 5

| Measurement item and pH at measurement | Field strength kV/cm | Sample | Application time and relative activity | | |
|---|---|---|---|---|---|
| | | | 22 hr (early stage of logarithmic phase) | 44 hr (latter stage of logarithmic phase) | 66 hr (stationary phase) |
| Acid phosphatase pH 5.0 | 15 | Extracellular | 91% | 107% | 105% |
| | 15 | Intracellular | 90% | 105% | 108% |
| Esterase pH 5.0 | 15 | Extracellular | — | 104% | 102% |
| | 15 | Intracellular | — | 95% | 98% |

Both the enzymes showed equivalent activity intracellularly and extracellularly, indicating that the application of the pulsed electric field did not improve the enzyme extraction efficiency from the cells, but affected the enzyme productivity.

(6) *Bacillus subtilis* JCM 1465 Strain (Study on Application Time and Field Strength)

The following test groups with different application times and field strengths of the pulsed electric field were set.

(a) A pulsed electric field having field strength of 15 kV/cm was applied 22 hours after culture (early stage of logarithmic phase).

(b) A pulsed electric field having field strength of 30 kV/cm was applied 22 hours after culture.

(c) A pulsed electric field having field strength of 15 kV/cm was applied 44 hours after culture (latter stage of logarithmic phase).

(d) A pulsed electric field having field strength of 30 kV/cm was applied 44 hours after the culture.

The culture solution was recovered 66 hours after culture to prepare a sample, and various enzyme activities were measured. The measurement results are shown in the following table. The underline represents an increase in activity, and the double underline represents a decrease in activity.

TABLE 6

| Measurement item and pH at measurement | Field strength kV/cm | Application time and relative activity | |
|---|---|---|---|
| | | 22 hr (early stage of logarithmic phase) | 44 hr (latter stage of logarithmic phase) |
| α-Amylase pH 5.0 | 15 | 87% | 103% |
| | 30 | 109% | 96% |
| α-Amylase pH 7.1 | 15 | 93% | 106% |
| | 30 | 106% | 94% |
| α-Amylase pH 9.2 | 15 | 92% | 92% |
| | 30 | 93% | 88% |
| α-Glucosidase pH 5.0 | 15 | 97% | 97% |
| | 30 | 98% | 96% |
| Protease pH 4.2 | 15 | 108% | 114% |
| | 30 | 121% | 110% |
| Protease pH 7.0 | 15 | 95% | 100% |
| | 30 | 108% | 109% |
| Protease pH 9.2 | 15 | 100% | 100% |
| | 30 | 106% | 101% |
| Leucine aminopeptidase pH 5.0 | 15 | 136% | 132% |
| | 30 | 154% | 132% |
| Alkaline phosphatase pH 9.2 | 15 | 96% | 99% |
| | 30 | 98% | 108% |
| Lipase pH 7.1 | 15 | 88% | 98% |
| | 30 | — | 106% |
| Lipase pH 9.2 | 15 | 74% | 89% |
| | 30 | 85% | 89% |

When the pulsed electric field was applied in the logarithmic phase, the production amount of the peptidase increased.

(7) *Bacillus amyloliquefaciens* IFO 3034 Strain (SCD Medium) (Study on Application Time and Field Strength)

The following test groups with different application times and field strengths of the pulsed electric field were set.

(a) A pulsed electric field having field strength of 15 kV/cm was applied 22 hours after culture (early stage of logarithmic phase).

(b) A pulsed electric field having field strength of 30 kV/cm was applied 22 hours after culture.

(c) A pulsed electric field having field strength of 15 kV/cm was applied 44 hours after culture (latter stage of logarithmic phase).

(d) A pulsed electric field having field strength of 30 kV/cm was applied 44 hours after the culture.

The culture solution was recovered 66 hours after culture to prepare a sample, and various enzyme activities were measured. The measurement results are shown in the following table. The underline represents an increase in activity, and the double underline represents a decrease in activity.

TABLE 7

| Measurement item and pH at measurement | Field strength kV/cm | Application time and relative activity | |
|---|---|---|---|
| | | 22 hr (early stage of logarithmic phase) | 44 hr (latter stage of logarithmic phase) |
| α-Amylase pH 5.0 | 15 | 86% | 98% |
| | 30 | 98% | 101% |
| α-Amylase pH 7.1 | 15 | 111% | 107% |
| | 30 | 120% | 102% |
| α-Amylase pH 9.2 | 15 | 85% | 96% |
| | 30 | 93% | 93% |
| α-Glucosidase pH 5.0 | 15 | 97% | — |
| | 30 | 101% | 97% |
| Protease pH 4.2 | 15 | 106% | 110% |
| | 30 | 111% | 114% |
| Protease pH 7.0 | 15 | 97% | 107% |
| | 30 | 98% | 104% |
| Protease pH 9.2 | 15 | 95% | 102% |
| | 30 | 94% | 102% |
| Leucine aminopeptidase pH 9.2 | 15 | 102% | 100% |
| | 30 | 107% | 102% |
| Alkaline phosphatase pH 9.2 | 15 | — | 75% |
| | 30 | 118% | 80% |
| Lipase pH 7.1 | 15 | 104% | 120% |
| | 30 | 101% | 108% |
| Lipase pH 9.2 | 15 | 104% | 129% |
| | 30 | 86% | 128% |

For the lipases, the enzyme production amount increased upon application of the pulsed electric field in the logarithmic phase.

(8) *Bacillus amyloliquefaciens* IFO 3034 Strain (YM Broth Medium) (Study on Application Time and Culture Medium)

The following test groups with different application times of the pulsed electric field were set.

(a) A pulsed electric field having field strength of 30 kV/cm was applied 21 hours after culture (early stage of logarithmic phase).

(b) A pulsed electric field having field strength of 30 kV/cm was applied 43 hours after culture (latter stage of logarithmic phase).

(c) A pulsed electric field having field strength of 30 kV/cm was applied 21 hours after culture and 43 hours after culture.

(d) A pulsed electric field having field strength of 30 kV/cm was applied 21 hours after culture, 43 hours after culture, and 65 hours after culture (stationary phase).

(e) A pulsed electric field having field strength of 30 kV/cm was applied 43 hours after culture and 65 hours after culture.

With respect to the test groups (a), (b), and (c), the culture solution was recovered 65 hours after culture to prepare a sample, and various enzyme activities were measured. The measurement results are shown in the following table.

TABLE 8

| Measurement item and pH at measurement | Field strength kV/cm | Application time and relative activity | | |
|---|---|---|---|---|
| | | 21 hr (early stage of logarithmic phase) | 43 hr (latter stage of logarithmic phase) | 21, 43 hr |
| α-Amylase pH 7.1 | 30 | 97% | 108% | 105% |
| β-Galactosidase pH 7.0 | 30 | 108% | 81% | 95% |
| Protease pH 5.0 | 30 | 119% | 109% | 105% |
| Protease pH 7.0 | 30 | 109% | 103% | 104% |
| Protease pH 9.2 | 30 | 116% | 99% | 95% |
| Lipase pH 9.2 | 30 | 97% | 92% | 116% |

On the other hand, with respect to the test groups (a), (c), (d), and (e), the culture solution was recovered 87 hours after culture to prepare a sample, and various enzyme activities were measured. The measurement results are shown in the following table. The double underline represents a decrease in activity.

TABLE 9

| Measurement item and pH at measurement | Field strength kV/cm | Application time and relative activity | | | |
|---|---|---|---|---|---|
| | | 21 hr (early stage of logarithmic phase) | 21, 43 hr | 21, 43, 65 hr | 43, 65 hr |
| α-Amylase pH 7.1 | 30 | 115% | 95% | 107% | 113% |
| β-Galactosidase pH 7.0 | 30 | 104% | 104% | 96% | 87% |
| Protease pH 5.0 | 30 | 99% | 97% | 94% | 89% |
| Protease pH 7.0 | 30 | 106% | 98% | 101% | 98% |
| Protease pH 9.2 | 30 | 89% | 90% | 77% | 80% |
| Cellulase pH 5.0 | 30 | 56% | 64% | 63% | 76% |
| Lipase pH 9.2 | 30 | 107% | 116% | 122% | 119% |

Similar results were obtained when the microorganisms were cultured in different media. For cellulase, the enzyme production amount decreased upon application of the pulsed electric field in the logarithmic phase. For lipase, the enzyme production amount increased by applying a pulsed electric field at multiple times.

(9) *Bacillus circulans* ATCC 21590 Strain (Study on Application Time)

The following test groups with different application times of the pulsed electric field were set.

(a) A pulsed electric field having field strength of 30 kV/cm was applied 43 hours after culture (early stage of logarithmic phase).

(b) A pulsed electric field having field strength of 30 kV/cm was applied 43 hours after culture and 65 hours after culture (latter stage of logarithmic phase).

With respect to the test group (a), the culture solution was recovered 65 hours after culture to prepare a sample, and various enzyme activities were measured. The measurement results are shown in the following table. The underline represents an increase in activity.

TABLE 10

| Measurement item and pH at measurement | Field strength kV/cm | Application time and relative activity 43 hr (early stage of logarithmic phase) |
|---|---|---|
| α-Amylase pH 7.1 | 30 | 96% |
| β-Galactosidase pH 7.0 | 30 | 128% |
| Protease pH 5.0 | 30 | 102% |
| Protease pH 7.0 | 30 | 103% |
| Protease pH 9.2 | 30 | 105% |

On the other hand, with respect to the test groups (a) and (b), the culture solution was recovered 87 hours after culture to prepare a sample, and various enzyme activities were measured. The measurement results are shown in the following table. The underline represents an increase in activity.

TABLE 11

| Measurement item and pH at measurement | Field strength kV/cm | Application time and relative activity | |
|---|---|---|---|
| | | 43 hr (early stage of logarithmic phase) | 43, 65 hr |
| α-Amylase pH 7.1 | 30 | 110% | 102% |
| β-Galactosidase pH 7.0 | 30 | 136% | 143% |
| Protease pH 5.0 | 30 | 104% | 92% |
| Protease pH 7.0 | 30 | 99% | 92% |
| Protease pH 9.2 | 30 | 115% | 102% |

For β-galactosidase, when the pulsed electric field was applied in the logarithmic phase, the enzyme production amount increased.

(10) *Streptomyces griseus* IFO 12875 Strain (Study on Application Time and Number of Applications)

The following test groups with different application times of the pulsed electric field and numbers of shots were set.

(a) A pulsed electric field having field strength of 30 kV/cm and a number of shots of 100 was applied 21 hours after culture (early stage of logarithmic phase).

(b) A pulsed electric field having field strength of 30 kV/cm and a number of shots of 400 was applied 21 hours after culture.

(c) A pulsed electric field having field strength of 30 kV/cm and a number of shots of 100 was applied 43 hours after culture (latter stage of logarithmic phase).

(d) A pulsed electric field having field strength of 30 kV/cm and a number of shots of 400 was applied 43 hours after the culture.

(e) A pulsed electric field having field strength of 30 kV/cm and a number of shots of 100 was applied 21 hours after culture and 43 hours after culture.

(f) A pulsed electric field having field strength of 30 kV/cm and a number of shots of 400 was applied 21 hours after culture and 43 hours after culture.

(g) A pulsed electric field having field strength of 30 kV/cm and a number of shots of 100 was applied 21 hours after culture, 43 hours after culture, and 65 hours after culture (stationary phase).

(h) A pulsed electric field having field strength of 30 kV/cm and a number of shots of 400 was applied 21 hours after culture, 43 hours after culture, and 65 hours after culture.

(i) A pulsed electric field having field strength of 30 kV/cm and a number of shots of 100 was applied 43 hours after culture and 65 hours after culture.

(j) A pulsed electric field having field strength of 30 kV/cm and a number of shots of 400 was applied 43 hours after culture and 65 hours after culture.

With respect to the test groups (a) to (f), the culture solution was recovered 65 hours after culture to prepare a sample, and various enzyme activities were measured. The measurement results are shown in the following table. The underline represents an increase in activity.

TABLE 12

| Measurement item and pH at measurement | Field strength kV/cm | Number of appli-cations | Application time and relative activity | | |
|---|---|---|---|---|---|
| | | | 21 hr (early stage of logarithmic phase) | 43 hr (latter stage of logarithmic phase) | 21, 43 hr |
| α-Amylase pH 7.1 | 30 | 100 | 95% | 93% | 105% |
| | 30 | 400 | — | 81% | — |
| Protease pH 5.0 | 30 | 100 | 128% | 102% | 104% |
| | 30 | 400 | — | 105% | — |
| Protease pH 7.0 | 30 | 100 | 120% | 107% | 108% |
| | 30 | 400 | — | 107% | — |
| Protease pH 9.2 | 30 | 100 | 119% | 107% | 109% |
| | 30 | 400 | — | 109% | — |

On the other hand, with respect to the test groups (a), (b), and (e) to (j), the culture solution was recovered 87 hours after culture to prepare a sample, and various enzyme activities were measured. The measurement results are shown in the following table. The underline represents an increase in activity, and the double underline represents a decrease in activity.

TABLE 13

| Measurement item and pH at measurement | Field strength kV/cm | Number of applications | Application time and relative activity | | | |
|---|---|---|---|---|---|---|
| | | | 21 hr (early stage of logarithmic phase) | 21, 43 hr | 21, 43, 65 hr | 43, 65 hr |
| α-Amylase pH 7.1 | 30 | 100 | 79% | 87% | 74% | 75% |
| | 30 | 400 | — | — | — | 59% |
| β-Glucosidase pH 7.0 | 30 | 100 | 139% | 150% | 147% | 108% |
| | 30 | 400 | — | — | — | 118% |
| Protease pH 5.0 | 30 | 100 | — | 97% | 100% | 89% |
| | 30 | 400 | — | — | — | 101% |

TABLE 13-continued

|  |  |  | Application time and relative activity | | | |
|---|---|---|---|---|---|---|
| Measurement item and pH at measurement | Field strength kV/cm | Number of applications | 21 hr (early stage of logarithmic phase) | 21, 43 hr | 21, 43, 65 hr | 43, 65 hr |
| Protease pH 7.0 | 30 | 100 | 109% | 101% | 93% | 94% |
|  | 30 | 400 | — | — | — | 106% |
| Protease pH 9.2 | 30 | 100 | 119% | 100% | 103% | 100% |
|  | 30 | 400 | — | — | — | 108% |

No significant difference due to the difference in number of shots was observed. When the pulsed electric field was applied from the logarithmic phase to the stationary phase, the production amount of the α-amylase decreased. For β-glucosidase, when the pulsed electric field was applied in the logarithmic phase, the enzyme production amount increased.

(11) *Streptomyces thermocarboxydus* JCM 10367 Strain (Study on Application Time and Number of Applications)

The following test groups with different application times of the pulsed electric field and numbers of shots were set.

(a) A pulsed electric field having field strength of 30 kV/cm and a number of shots of 100 was applied 21 hours after culture (early stage of logarithmic phase)

(b) A pulsed electric field having field strength of 30 kV/cm and a number of shots of 400 was applied 21 hours after culture.

(c) A pulsed electric field having field strength of 30 kV/cm and a number of shots of 100 was applied 43 hours after culture (latter stage of logarithmic phase).

(d) A pulsed electric field having field strength of 30 kV/cm and a number of shots of 400 was applied 43 hours after the culture.

(e) A pulsed electric field having field strength of 30 kV/cm and a number of shots of 100 was applied 21 hours after culture and 43 hours after culture.

(f) A pulsed electric field having field strength of 30 kV/cm and a number of shots of 400 was applied 21 hours after culture and 43 hours after culture.

(g) A pulsed electric field having field strength of 30 kV/cm and a number of shots of 100 was applied 21 hours after culture, 43 hours after culture, and 65 hours after culture (stationary phase).

(h) A pulsed electric field having field strength of 30 kV/cm and a number of shots of 400 was applied 21 hours after culture, 43 hours after culture, and 65 hours after culture.

(i) A pulsed electric field having field strength of 30 kV/cm and a number of shots of 100 was applied 43 hours after culture and 65 hours after culture.

(j) A pulsed electric field having field strength of 30 kV/cm and a number of shots of 400 was applied 43 hours after culture and 65 hours after culture.

With respect to the test groups (a) to (f), the culture solution was recovered 65 hours after culture to prepare a sample, and various enzyme activities were measured. The measurement results are shown in the following table. The underline represents an increase in activity.

TABLE 14

|  |  |  | Application time and relative activity | | |
|---|---|---|---|---|---|
| Measurement item and pH at measurement | Field strength kV/cm | Number of applications | 21 hr (early stage of logarithmic phase) | 43 hr (latter stage of logarithmic phase) | 21, 43 hr |
| α-Amylase pH 7.1 | 30 | 100 | 95% | 93% | 105% |
|  | 30 | 400 | — | 81% | — |
| Protease pH 5.0 | 30 | 100 | <u>127%</u> | 104% | 114% |
|  | 30 | 400 | — | 107% | — |
| Protease pH 7.0 | 30 | 100 | 122% | 103% | 111% |
|  | 30 | 400 | — | 104% | — |
| Protease pH 9.2 | 30 | 100 | 124% | 106% | 116% |
|  | 30 | 400 | — | 106% | — |

On the other hand, with respect to the test groups (a), (b), and (e) to (j), the culture solution was recovered 87 hours after culture to prepare a sample, and various enzyme activities were measured. The measurement results are shown in the following table. The underline represents an increase in activity.

TABLE 15

|  |  |  | Application time and relative activity | | | |
|---|---|---|---|---|---|---|
| Measurement item and pH at measurement | Field strength kV/cm | Number of applications | 21 hr (early stage of logarithmic phase) | 21, 43 hr | 21, 43, 65 hr | 43, 65 hr |
| α-Amylase pH 7.1 | 30 | 100 | 105% | 105% | 97% | 100% |
|  | 30 | 400 | — | — | — | 93% |
| Protease pH 5.0 | 30 | 100 | — | 112% | 106% | 105% |
|  | 30 | 400 | — | — | — | 95% |
| Protease pH 7.0 | 30 | 100 | <u>149%</u> | 112% | 103% | 111% |
|  | 30 | 400 | — | — | — | 106% |
| Protease pH 9.2 | 30 | 100 | <u>153%</u> | 115% | 111% | 116% |
|  | 30 | 400 | — | — | — | 112% |

No significant difference due to the difference in number of shots was observed. For the proteases, the enzyme production amount increased upon application of the pulsed electric field in the logarithmic phase.

As described above, it was possible to change the enzyme productivity of various microorganisms upon application of the pulsed electric field. In other words, the application of a pulsed electric field was demonstrated to be effective as a means to control the enzyme productivity of microorganisms.

INDUSTRIAL APPLICABILITY

The present invention using a pulsed electric field to control the enzyme productivity of microorganisms is a general-purpose technique applicable to various microorganisms and various enzymes. According to the present invention, an enzyme composition and an enzyme preparation each having a target enzyme formulation (that is, with controlled enzyme formulation) can be obtained by increasing the production amount of a specific enzyme or inhibiting the production amount of a specific enzyme.

The present invention is not limited to the description of the embodiments and examples of the present invention at all. Various modifications that can be easily achieved by those skilled in the art without departing from the claims also fall within the scope of the invention. The contents of the articles, the patent laid-open publications, patent publications, and the like specified herein shall be cited by incorporation in their entity.

The invention claimed is:

1. A method for controlling the enzyme productivity of a microorganism comprising applying a pulsed electric field to a microorganism,
    wherein the pulsed electric field is applied to a culture solution during culture of the microorganism,
    wherein a field strength of the pulsed electric field is 10 kV/cm to 50 kV/cm, and
    wherein a pulse waveform of the pulsed electric field is a damped oscillation waveform.

2. The method according to claim 1, wherein the culture solution circulates in an electrode part that generates the pulsed electric field during culture.

3. The method according to claim 1, wherein the pulsed electric field is repeatedly applied during culture.

4. The method according to claim 1, wherein a production amount of one or more enzymes selected from the group consisting of amylase, glucosidase, galactosidase, cellulase, esterase, lipase, protease, phosphatase, peptidase, nuclease, deaminase, oxidase, dehydrogenase, glutaminase, pectinase, catalase, dextranase, transglutaminase, protein deamidase, and pullulanase is controlled.

5. The method according to claim 1, wherein a production amount of one or more enzymes selected from the group consisting of α-amylase, α-glucosidase, β-glucosidase, α-galactosidase, β-galactosidase, cellulase, esterase, lipase, protease, acid phosphatase, alkaline phosphatase, leucine peptidase, alanine aminopeptidase, PPL aminopeptidase, and SAPA aminopeptidase is controlled.

6. The method according to claim 1, wherein the microorganism is a microorganism selected from the group consisting of filamentous fungi, actinomycetes, yeast, and bacteria.

7. The method according to claim 1, wherein the microorganism is a microorganism selected from the group consisting of the genus *Aspergillus*, the genus *Mucor*, the genus *Rhizomucor*, the genus *Rhizopus*, the genus *Penicillium*, the genus *Trametes*, the genus *Streptomyces*, the genus *Candida*, the genus *Saccharomyces*, the genus *Sporobolomyces*, the genus *Kluyveromyces*, the genus *Pichia*, the genus *Cryptococcus*, the genus *Bacillus*, the genus *Streptococcus*, the genus *Pseudomonas*, the genus *Burkholderia*, the genus *Clostridium*, the genus *Myrothecium*, the genus *Klebsiella*, the genus *Chryseobacterium*, and the genus *Escherichia*.

8. The method according to claim 1, wherein the microorganism is a microorganism selected from the group consisting of *Aspergillus oryzae*, *Aspergillus niger*, *Mucor javanicus*, *Bacillus subtilis*, *Bacillus amyloliquefaciens*, *Bacillus circulans*, *Streptomyces griseus*, and *Streptomyces thermocarboxydus*.

9. The method according to claim 1, wherein a control of the enzyme productivity is any of the following (1) to (8):
    (1) control in which the microorganism is *Aspergillus oryzae*, the application of the pulsed electric field is carried out in a logarithmic phase and/or stationary phase during culture, and the production amount of one or more enzymes selected from the group consisting of α-amylase, α-galactosidase, β-galactosidase, protease, leucine aminopeptidase, PPL aminopeptidase, and esterase is up-regulated; control in which the application of the pulsed electric field is carried out in an induction phase during culture, and the production amount of one or more enzymes selected from the group consisting of α-amylase, α-glucosidase, β-glucosidase, α-galactosidase, leucine aminopeptidase, and esterase is down-regulated; or control in which the application of the pulsed electric field is carried out in the logarithmic phase and/or stationary phase during culture, and the production amount of SAPA aminopeptidase is down-regulated;
    (2) control in which the microorganism is *Aspergillus niger*, the application of the pulsed electric field is carried out in the stationary phase during culture, and the production amount of α-amylase and/or protease is up-regulated;
    (3) control in which the microorganism is *Mucor javanicus*, the application of the pulsed electric field is carried out in the logarithmic phase and/or stationary phase during culture, and the production amount of α-amylase and/or β-glucosidase is up-regulated;
    (4) control in which the microorganism is *Bacillus subtilis*, the application of the pulsed electric field is carried out in the logarithmic phase during culture, and the production amount of leucine aminopeptidase is up-regulated;
    (5) control in which the microorganism is *Bacillus amyloliquefaciens*, the application of the pulsed electric field is carried out in the logarithmic phase and/or stationary phase during culture, and the production amount of lipase is up-regulated or the production amount of cellulase is down-regulated;
    (6) control in which the microorganism is *Bacillus circulans*, the application of the pulsed electric field is carried out in the logarithmic phase during culture, and the production amount of β-galactosidase is up-regulated;
    (7) control in which the microorganism is *Streptomyces griseus*, the application of the pulsed electric field is carried out in the logarithmic phase and/or stationary phase during culture, and the production amount of β-glucosidase is up-regulated or the production amount of α-amylase is down-regulated; and
    (8) control in which the microorganism is *Streptomyces thermocarboxydus*, the application of the pulsed electric field is carried out in the logarithmic phase during culture, and the production amount of protease is up-regulated.

10. The method according to claim 1, wherein the application of the pulsed electric field is carried out in the induction phase during culture, and the production amount of β-galactosidase is up-regulated.

11. The method according to claim 1, wherein the application of the pulsed electric field is carried out in the logarithmic phase during culture, and the production amount of one or more enzymes selected from the group consisting of α-amylase, α-galactosidase, β-glucosidase, β-galactosidase, protease, leucine peptidase, PPL aminopeptidase, and lipase is up-regulated.

12. The method according to claim 1, wherein the application of the pulsed electric field is carried out in the stationary phase during culture, and the production amount of α-amylase and/or protease is up-regulated.

13. The method according to claim 1, wherein the microorganism is *Aspergillus oryzae*, the application of the pulsed electric field is carried out in the logarithmic phase during culture, and the production amount of protease is up-regulated.

14. The method according to claim 1, wherein the microorganism is *Aspergillus oryzae*, the application of the pulsed electric field is carried out in the logarithmic phase during culture, and the production amount of peptidase is up-regulated.

15. The method according to claim 1, wherein the microorganism is *Aspergillus oryzae*, the application of the pulsed electric field is carried out in the induction phase and/or logarithmic phase during culture, and the production amount of β-galactosidase is up-regulated.

16. The method according to claim 1, wherein the microorganism is *Aspergillus oryzae*, the application of the pulsed electric field is carried out in the logarithmic phase during culture, and the production amount of α-galactosidase is up-regulated.

17. The method according to claim 1, wherein the microorganism is *Aspergillus oryzae*, the application of the pulsed electric field is carried out in the logarithmic phase during culture, and the production amount of α-amylase is up-regulated.

18. The method according to claim 1, wherein the microorganism is *Aspergillus niger*, the application of the pulsed electric field is carried out in the stationary phase during culture, and the production amount of protease is up-regulated.

19. The method according to claim 1, wherein the microorganism is *Aspergillus niger*, the application of the pulsed electric field is carried out in the stationary phase during culture, and the production amount of α-amylase is up-regulated.

20. The method according to claim 1, wherein the microorganism is *Bacillus subtilis*, the application of the pulsed electric field is carried out in the logarithmic phase during culture, and the production amount of peptidase is up-regulated.

21. The microorganism according to claim 1, wherein the microorganism is *Bacillus circulans*, the application of the pulsed electric field is carried out in the logarithmic phase during culture, and the production amount of β-galactosidase is up-regulated.

* * * * *